United States Patent
Moturu et al.

(10) Patent No.: US 10,102,341 B2
(45) Date of Patent: Oct. 16, 2018

(54) METHOD FOR MANAGING PATIENT QUALITY OF LIFE

(71) Applicant: Ginger.io, Inc., San Francisco, CA (US)

(72) Inventors: Sai Moturu, San Francisco, CA (US); Anmol Madan, San Francisco, CA (US)

(73) Assignee: Ginger.io, Inc., San Francisco, CA (US)

(*) Notice: Subject to any disclaimer, the term of this patent is extended or adjusted under 35 U.S.C. 154(b) by 440 days.

(21) Appl. No.: 14/934,893

(22) Filed: Nov. 6, 2015

(65) Prior Publication Data

US 2016/0063205 A1 Mar. 3, 2016

Related U.S. Application Data

(63) Continuation-in-part of application No. 13/969,339, filed on Aug. 16, 2013.

(60) Provisional application No. 61/683,867, filed on Aug. 16, 2012, provisional application No. 61/683,869, filed on Aug. 16, 2012, provisional application No. 62/076,445, filed on Nov. 6, 2014, provisional application No. 62/094,583, filed on Dec. 19, 2014.

(51) Int. Cl.
*G06F 19/00* (2018.01)
*G16H 50/50* (2018.01)
*G16H 10/20* (2018.01)

(52) U.S. Cl.
CPC .......... *G06F 19/3418* (2013.01); *G06F 19/00* (2013.01); *G16H 50/50* (2018.01); *G06F 19/3456* (2013.01); *G16H 10/20* (2018.01)

(58) Field of Classification Search
None
See application file for complete search history.

(56) References Cited

U.S. PATENT DOCUMENTS

| 7,188,151 | B2 | 3/2007 | Kumar et al. |
| 7,248,677 | B2 | 7/2007 | Randall et al. |
| 7,761,309 | B2 | 7/2010 | Sacco et al. |
| 2004/0225340 | A1 | 11/2004 | Evans |

(Continued)

FOREIGN PATENT DOCUMENTS

| CN | 101600008 A | 12/2009 |
| WO | 2008085308 A1 | 7/2008 |

(Continued)

*Primary Examiner* — Michael Tomaszewski
(74) *Attorney, Agent, or Firm* — Jeffrey Schox; Brian Lao

(57) ABSTRACT

A method and system for modeling behavior and pain-related state of an individual, the method comprising: receiving a log of use dataset associated with communication behavior of the individual during a time period; receiving a supplementary dataset characterizing activity of the individual during the time period; receiving a survey dataset including responses, to at least one of a set of symptom-assessment surveys, associated with a set of time points of the time period; generating a predictive analysis of a pain-related state of the individual associated with at least a portion of the time period, from at least one of the log of use dataset, the supplementary dataset, and the survey dataset; and generating an alert upon detection that a set of parameters from the predictive analysis of the pain-related state satisfy a threshold condition.

20 Claims, 6 Drawing Sheets

(56) References Cited

U.S. PATENT DOCUMENTS

| | | |
|---|---|---|
| 2005/0108051 A1 | 5/2005 | Weinstein |
| 2007/0094048 A1* | 4/2007 | Grichnik ................ G06Q 50/22 |
| | | 705/2 |
| 2007/0226012 A1 | 9/2007 | Salgado et al. |
| 2007/0288266 A1 | 12/2007 | Sysko et al. |
| 2009/0125333 A1 | 5/2009 | Heywood et al. |
| 2010/0082367 A1* | 4/2010 | Hains ................ G06F 19/3456 |
| | | 705/2 |
| 2010/0203876 A1 | 8/2010 | Krishnaswamy |
| 2011/0009715 A1 | 1/2011 | Karplus et al. |
| 2011/0066036 A1 | 3/2011 | Zilca et al. |
| 2011/0184250 A1 | 7/2011 | Schmidt et al. |
| 2013/0117040 A1 | 5/2013 | James et al. |
| 2013/0297536 A1* | 11/2013 | Almosni ................ G16H 50/20 |
| | | 706/12 |
| 2014/0039914 A1 | 2/2014 | Dansereau et al. |

FOREIGN PATENT DOCUMENTS

| | | |
|---|---|---|
| WO | 2008096634 A1 | 8/2008 |
| WO | 2012025622 A2 | 3/2012 |
| WO | 2015003247 A1 | 1/2015 |

\* cited by examiner

METHOD FOR MANAGING PATIENT QUALITY OF LIFE

CROSS-REFERENCE TO RELATED APPLICATIONS

This application is a continuation-in-part application of U.S. application Ser. No. 13/969,339 filed 16 Aug. 2013, which claims the benefit of U.S. Provisional Application Ser. No. 61/683,867 filed on 16 Aug. 2012 and U.S. Provisional Application Ser. No. 61/683,869 filed on 16 Aug. 2012, which are each incorporated in its entirety herein by this reference.

This application also claims the benefit of U.S. Provisional Application Ser. No. 62/076,445 filed 6 Nov. 2014, and U.S. Provisional Application Ser. No. 62/094,583 filed 19 Dec. 2014, which are each incorporated in its entirety herein by this reference.

TECHNICAL FIELD

This invention relates generally to the field of patient health and more specifically to a new and useful method for modeling behavior and pain-related states in the field of patient health.

BACKGROUND

Rheumatic diseases are painful conditions characterized by inflammation and swelling in the joints and/or muscles. Almost any joint can be affected by one of 100s of rheumatic diseases (e.g., degenerative arthropathies, inflammatory arthropathies, systemic conditions, connective tissue diseases, soft tissue rheumatism, etc.), which can significantly interfere with a person's ability to work, sleep, maintain desired levels of physical activity due to joint pain and instability, and enjoy once-pleasurable activities. Given that injuries and aging both contribute to progression of rheumatic diseases, and that over 20% of adults over the age of 18 suffer from some form of rheumatic disease in the U.S. alone, efforts to detect rheumatic disease at early stages, determine critical time points at which intervention would be most effective, and generate measures for monitoring of progress in rheumatoid disease treatment should be actively pursued. Furthermore, rheumatic diseases and other conditions (e.g., musculoskeletal conditions, conditions resulting in chronic pain, conditions producing acute pain symptoms, etc.) can contribute to reduced quality of life for individuals, as attributed to pain symptoms and/or loss of function. Furthermore, many other conditions can contribute to pain and/or reduced function, thereby causing a reduction in quality of life.

Unfortunately, current standards of detection, diagnosis, treatment, and monitoring of rheumatic disorders, musculoskeletal disorders, and/or other conditions that reduce quality of life due to pain and/or reduced function are responsible for delays in diagnoses of disorders and non-optimal treatment methodologies, which fail to adequately slow or stop disease progression. Furthermore, patients often contribute to a delay between exhibition of symptoms and treatment, for instance, by seeking help long after initiation of pain symptoms. For patients with high pain tolerances, a visit to the doctor may not occur until pain surpasses an unnecessarily high threshold, by which time the pain-related disorder has progressed unnecessarily. Patients may also tolerate chronic pain symptoms for an unnecessary amount of time before seeking help. As such, patient behavior can contribute to a rapid progression of disease state prior to treatment. While some delays are due to patient-induced factors, standards of detection diagnosis are severely deficient in many controllable aspects. In addition to these deficiencies, further limitations in detection, diagnosis, treatment, and/or monitoring of patient progress during treatment prevent adequate care of patients with diagnosable and treatable conditions.

As such, there is a need in the field of patient health for a new and useful method for modeling behavior and improving quality of life for a patient. This invention creates such a new and useful method for modeling behavior and improving quality of life for a patient.

DESCRIPTION OF THE EMBODIMENTS

The following description of the embodiments of the invention is not intended to limit the invention to these embodiments, but rather to enable any person skilled in the art to make and use this invention.

1. Method

Figure 1:
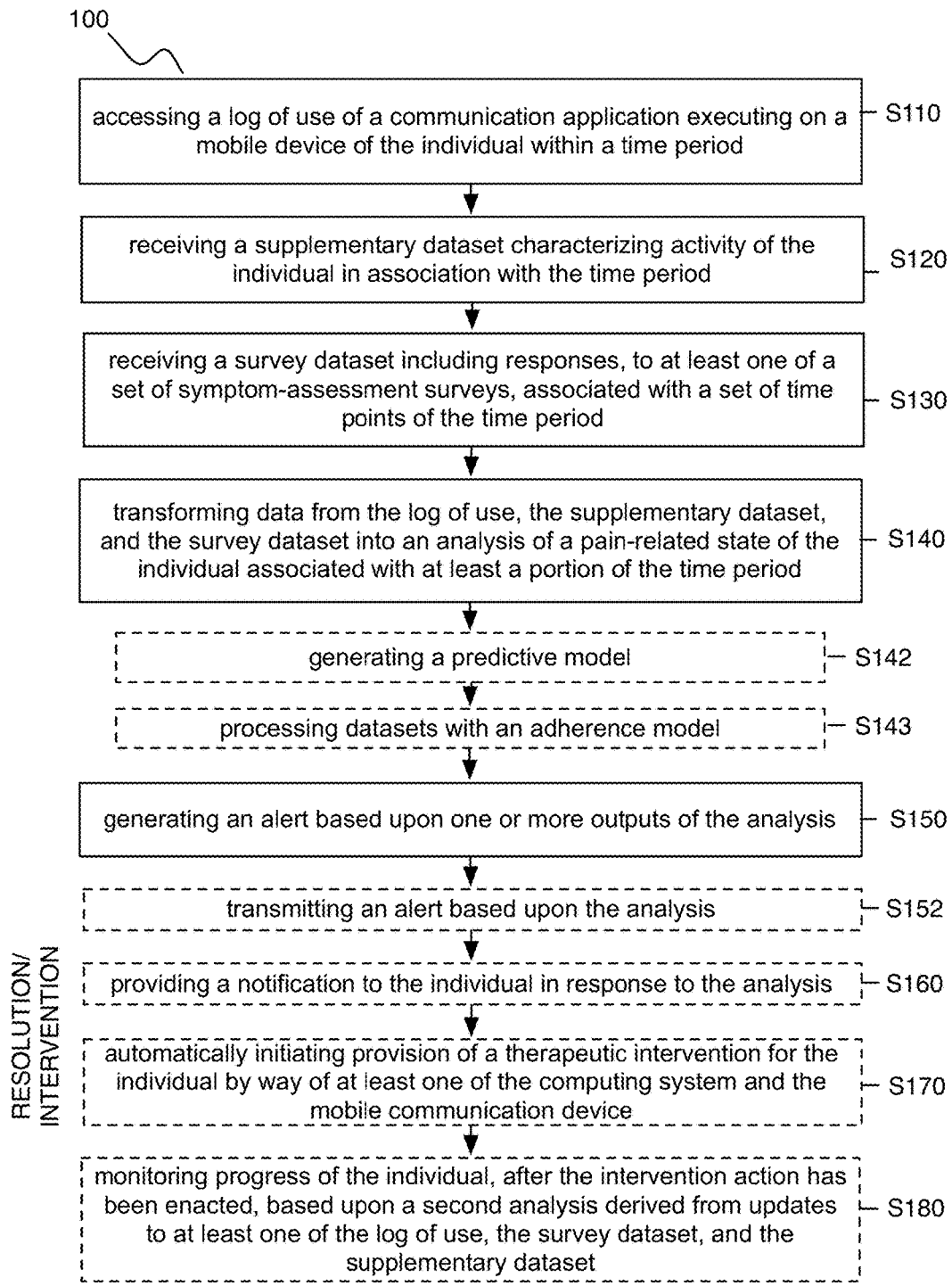
FIG. 1 is a flowchart of an embodiment of a method for modeling behavior and improving quality of life for an individual.

As shown in FIG. 1, a method 100 for managing pain of an individual includes: accessing a log of use of a communication application executing on a mobile device of the individual within a time period S110; receiving a supplementary dataset characterizing activity of the individual in association with the time period S120; receiving a survey dataset including responses, to at least one of a set of symptom-assessment surveys, associated with a set of time points of the time period, from the individual S130; for at least a time point of the set of time points, transforming data from the log of use, the supplementary dataset, and the survey dataset into an analysis of a pain-related state of the individual associated with at least a portion of the time period S140; and generating an alert based upon one or more outputs of the analysis S150. In some variations, the method 100 can further include any one or more of: providing a notification to the individual, at the mobile device, in response to the analysis S160; and automatically initiating provision of a therapeutic intervention for the individual by way of at least one of the computing system, the mobile communication device, and a caretaker computing device S170. In some variations, the method 100 can further include monitoring progress of the patient, after the intervention action has been enacted, based upon a second analysis derived from updates to at least one of the log of use, the survey dataset, and the supplementary dataset S180.

The method 100 functions to analyze communication behavior and other information regarding an individual (e.g., patient, user, at-risk individual) exhibiting symptoms of or diagnosed with a disorder contributing to increased pain and/or reduction of function (e.g., in terms of mobility, in terms of depression, in terms of fatigue, in terms of sleep disturbances, etc.), in order to identify when the patient enters a state at which intervention (e.g., treatment of symptoms, treatment of disease cause) would be most effective. As such, the method 100 can facilitate monitoring of states of disease progression (e.g., rheumatic disease progression, chronic pain progression, musculoskeletal disorder progression, etc.) in a patient, by enabling detection of changes in the patient's condition. In a specific application, the method 100 can monitor and analyze communication behavior, mobility behavior, and/or other behavior detected from any other suitable sensor(s) associated with a patient with a rheumatic disease, musculoskeletal disorder, or other condition causing pain over time, and promote interventions (e.g., pain-reduction treatments, immobilization, surgical procedures, etc.) to the individual and/or to an entity associated with the individual upon detection that the individual has entered or is at risk of entering a critical pain-related state (e.g., a pain-related associated with a disorder). Thus, the method 100 can provide a predictive model for one or more individual experiencing symptoms of pain, as well as an intervention model for providing interventions at key time points, to optimize improvement in patient outcomes (e.g., as exhibited by an improved state). The intervention model can thus implement an anticipated state to drive automated or manual targeted intervention for an individual (e.g., by making a doctor's appointment, by recommending immobilization, by recommending nerve stimulation treatment, by recommending a dietary supplement, by recommending medication, by recommending a surgical procedure, by performing electronic communication, by performing electronic device-based messaging, by providing other electronic device-based notifications, etc.) in some applications. In further embodiments, an analysis of the method 100 can be used to generate and/or provide therapeutic regimens to the individual as a therapeutic measure in slowing or stopping progression of a pain or function-related disorder of the individual.

While the method 100 can be implemented for a single individual exhibiting symptoms of a disorder, the method 100 can additionally or alternatively be implemented for a population of individuals (e.g., including the individual, excluding the individual), wherein the population of individuals can include individuals similar to and/or dissimilar to the individual (e.g., in type of disorder, in demographic group, in medical condition, in level of activity, etc.). Thus, information derived from the population of individuals can be used to provide additional insight into connections between the individual's behavior and risk of entering one of a spectrum of states of a specific disorder (e.g., rheumatic disorder, etc.), due to aggregation of data from a population of individuals.

The method 100 can further be applied to any suitable form of rheumatic disorder (e.g., degenerative arthropathies, inflammatory arthropathies, systemic conditions, connective tissue diseases, soft tissue rheumatism), and in some examples, can be applied to patients exhibiting symptoms associated with one or more of: osteoarthritis (OA), rheumatoid arthritis (RA), spondyloarthropathies (e.g., ankylosing spondylitis, reactive arthritis, psoriatic arthropathy, eteropathic spondylitis, etc.), Juvenile Idiopathic Arthritis, crystal arthropathies (e.g., gout, pseudogout), septic arthritis, lupus, Sjögren's syndrome, scleroderma, polymyositis, dermatomyositis, polymyalgia rheumatic, mixed connective tissue disease, polychondritis, sarcoidosis, vasculitis-related disorders, tennis elbow, golfer's elbow, bursitis, and any other rheumatic disorder. Additionally or alternatively, the method 100 can be applied to any suitable form of musculoskeletal disorder (e.g., fibromyalgia), and/or any condition contributing to increased pain or reduced function. Variations of the specific method 100 can thus screen for populations of specific demographics, disease states, and behavioral tendencies.

In a first specific example, the method 100 involves a population of patients with an average age of 53.7 years of age (e.g., with patients between 18 and 80 years of age), a body mass index between 12 and 48, and exhibiting symptoms or diagnosed with one of rheumatoid arthritis, osteoarthritis, systemic lupus erythematosus, and fibromyalgia. The population also included an approximately 10-20% male subpopulation, with a majority of married individuals, a majority of employed individuals, and a minority of substance (e.g., cigarette) users. In a second specific example, the method 100 involves a population of patients with an average age of 53.7 years of age (e.g., with patients between 18 and 80 years of age), a comorbidity index from 0-9 (e.g., with a mean of 2.5 and a standard deviation of 1.8), a body mass index between 12 and 48, and exhibiting symptoms or diagnosed with one of rheumatoid arthritis, osteoarthritis, systemic lupus erythematosus, and fibromyalgia. The population also included an approximately 10-20% male subpopulation, with a majority of married individuals, a majority of employed individuals, a majority of Caucasian individuals, and a minority of substance (e.g., cigarette) users.

However, variations of the specific example can alternatively include or filter patients of any other suitable demographic or condition. For instance, variations of the specific example can omit patients characterized by obesity, wherein promoting weight loss to healthy ranges often reduces or eliminates symptoms associated with a rheumatic disorder. However, patient populations for variations of the method 100 can additionally or alternatively be selected in any other suitable manner.

The method 100 is preferably implemented at least in part by an embodiment of the system 200 described in Section 2 below, variations of which can be implemented at least in part by embodiments, variations, and examples of the system described in U.S. application Ser. No. 13/969,339 entitled "Method for Modeling Behavior and Health Changes" and filed on 16 Aug. 2013; however, the method 100 can alternatively be implemented using any other suitable system configured to process communication and/or other behavior of the patient, in aggregation with other information, in order to generate a model of behavior and pain-related state in the patient.

1.1 Method—Passive Data

Block S110 recites: accessing a log of use of a communication application (e.g., native communication application) executing on a mobile device by the individual within a time period, which functions to unobtrusively collect and/or retrieve communication-related data from an individual's mobile device. Preferably, Block S110 is implemented using a module of a processing subsystem configured to interface with a native data collection application executing on a mobile device (e.g., smartphone, tablet, personal data assistant (PDA), personal music player, vehicle, head-mounted wearable computing device, wrist-mounted wearable computing device, etc.) of the individual, in order to retrieve communication data associated with communication-related interactions of the individual. As such, in one variation, a native data collection application can be installed on the mobile device of the patient, can execute substantially continuously while the mobile device is in an active state (e.g., in use, in an on-state, in a sleep state, etc.), and can record communication parameters (e.g., communication times, durations, contact entities) of each inbound and/or outbound communication from the mobile device. In implementing Block S110, the mobile device can then upload this data to a database (e.g., remote server, cloud computing system, storage module), at a desired frequency (e.g., in near real-time, every hour, at the end of each day, etc.) to be accessed by the processing subsystem/computing system described in more detail below. In one example of Block S110, the native data collection application can launch on the individual's mobile device as a background process that gathers data once the individual logs into an account, wherein the data includes how and with what frequency the individual interacts with and communicates with other individuals through phone calls, e-mail, instant messaging, an online social network, and any other suitable form of communication, parameters of which can be electronically logged.

As such, in accessing the log of use of the communication application, Block S110, preferably enables collection of one or more of: phone call-related data (e.g., number of sent and/or received calls, call duration, call start and/or end time, location of patient before, during, and/or after a call, and number of and time points of missed or ignored calls); text messaging (e.g., SMS test messaging) data (e.g., number of messages sent and/or received, message length associated with a contact of the individual, message entry speed, delay between message completion time point and sending time point, message efficiency, message accuracy, time of sent and/or received messages, location of the patient when receiving and/or sending a message); data on textual messages sent through other communication venues (e.g., public and/or private textual messages sent to contacts of the patient through an online social networking system, reviews of products, services, or businesses through an online ranking and/or review service, status updates, "likes" of content provided through an online social networking system), vocal and textual content (e.g., text and/or voice data that can be used to derive features indicative of negative or positive sentiments) and any other suitable type of data.

Figure 2:
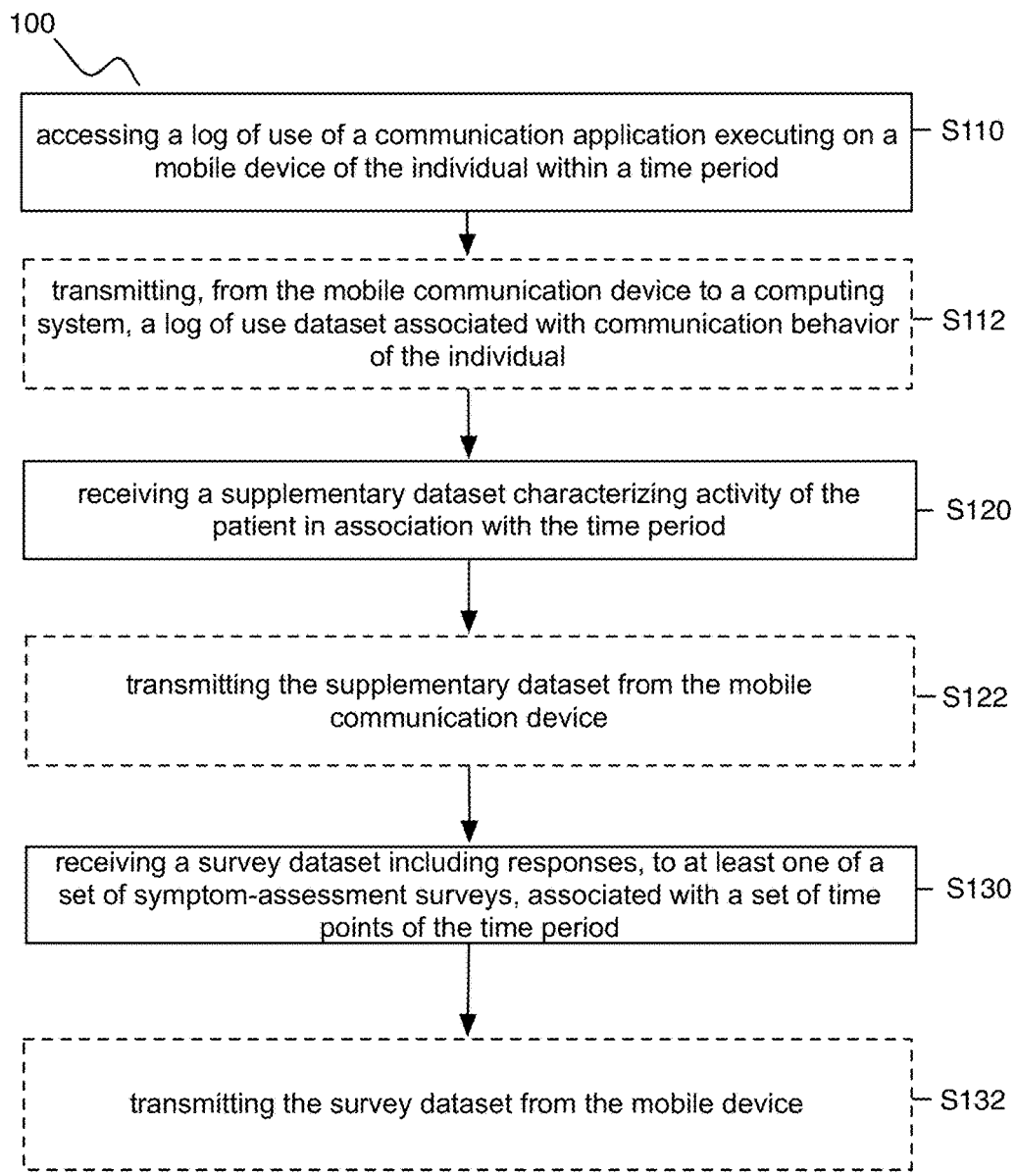
FIG. 2 is a flowchart of a variation of a portion of a method for modeling behavior and improving quality of life for an individual.

In relation to accessing the log of communication, Block S110 can include accessing the log of use at the mobile device of the individual, and transmitting, from the mobile device to a computing system, a log of use dataset associated with communication behavior of the individual S112, as shown in FIG. 2. As such, Block S110 can comprise establishing communication between the computing system and a communication module of the mobile device of the individual, wherein the communication module comprises hardware elements that collect and/or aggregate data associated with communication behavior of the individual. The communication module can thus be accessed (with or without appropriate security aspects) by one or more other portions of the system implementing the method 100, in order to retrieve and process log of use data, according to additional Blocks of the method 100 (described in more detail below). The computing system can be implemented in one or more of a processing module of the mobile device, a personal computer, a remote server, a cloud-based computing system, a computing module of any other suitable computing device (e.g., mobile computing device, wearable computing device, etc.), and any other suitable computing module. In transmitting the log of use dataset, a communication module (e.g., a hardware communication module associated with the communication application) can transmit data to the computing system by way of a wired and/or wireless data link (e.g., a communicable link over Bluetooth, a communicable link over Bluetooth LTE, etc.). However, Block S110 can include another other suitable variation of accessing the log of communication, transmitting data from the log of communication, and/or receiving a log of use dataset.

Block S120 recites: receiving a supplementary dataset characterizing activity of the individual in association with the time period, which functions to unobtrusively receive non-communication-related data from a patient's mobile communication device and/or other device configured to receive contextual data from the patient. Block S120 can include receiving non-communication-related data pertaining to the individual before, during, and/or after (or in the absence of) communication with another individual (e.g., a phone call) and/or computer network (e.g., a social networking application), as described above in relation to Block S110. Block S120 can include receiving one or more of: location information, movement information (e.g., related to physical isolation, related to lethargy), device usage information (e.g., screen usage information related to disturbed sleep, restlessness, and/or interest in mobile device activities), and any other suitable information. In variations, Block S120 can include receiving location information of the individual by way of one or more of: receiving a GPS location of the individual (e.g., from a GPS sensor within the mobile communication device of the individual), estimating the location of the individual through triangulation of local cellular towers in communication with the mobile communication device, identifying a geo-located local Wi-Fi hotspot during a phone call, and in any other suitable manner. In applications, data received in Block S110 and S120 can be processed to track behavior characteristics of the individual, such as mobility, periods of isolation, quality of life (e.g., work-life balance based on time spent at specific locations), periods of disrupted sleep, and any other location-derived behavior information.

As such, data from Blocks S110 and S120 can be merged (e.g., features extracted from outputs of Blocks S110 and S120 can be co-processed or otherwise combined) in subsequent blocks of the method 100 to track the individual's mobility during a communication, for instance, in the analysis of Block S140. In variations, Block S120 can additionally or alternatively include receiving mobile usage data, including data indicative of screen unlocks and mobile application usage (e.g., by retrieving usage information from mobile operating system logs, by retrieving usage information from a task manager on a mobile communication device, etc.). Blocks S120 and/or S110 can therefore facilitate tracking of variations and periods of activity/inactivity for a patient through automatically collected data (e.g., from the patient's mobile communication device), in order to enable identification of periods of activity and inactivity by the individual (e.g., extended periods when the individual was hyperactive on the device or not asleep).

In additional variations, Block S120 can additionally or alternatively include receiving one or more of: physical activity- or physical action-related data (e.g., accelerometer data, gyroscope data, data from an M7 or M8 chip) of the individual, local environmental data (e.g., climate data, temperature data, light parameter data, etc.), nutrition or diet-related data (e.g., data from food establishment check-ins, data from spectrophotometric analysis, etc.) of the individual, biometric data (e.g., data recorded through sensors within the individual's mobile device, data recorded through a wearable or other peripheral device in communication with the individual's mobile device) of the individual, and any other suitable data. In more detail, variations of biometric signals that can contribute to features (e.g., features indicative of pain/reduced function) processed/analyzed according to blocks of the method 100 can include any one or more of: electromyograph (EMG) signals, electrocardiography (ECG) signals, electroencephalograph (EEG) signals, galvanic skin response (GSR) signals, bioelectrical impedance (BIA) signals, any other suitable bioelectrical signal of the individual, respiration signals, body temperature, and any other suitable biometric information of the individual. Furthermore, environmental sensors (e.g., temperature sensors, air-quality sensors, ambient light sensors, etc.) can provide contextual information from the environment of the individual to provide additional supplemental data. In examples, one or more of an accelerometer (e.g., multi-axis accelerometer) and a gyroscope (e.g., multi-axis gyroscope) of a mobile computing device of the patient can be configured to enable detection of changes in gait of a patient exhibiting osteoarthritis symptoms, and to transmit data to a processing subsystem implementing portions of the method 100; thus, Block S130 can include receiving this data to further augment analyses performed in Block S140.

In relation to receiving data, Blocks S120 and/or S110 can additionally or alternatively include receiving data pertaining to individuals in contact with the individual during the period of time, such that data from the individual who experiences states of pain, reduced function, and/or overall reduced quality of life, and data from others in communication with the individual are received (e.g., using information from an analogous application executing on the electronic device(s) of others in communication with the individual). As such, Blocks S120 and/or S110 can provide a holistic view that aggregates communication behavior data and contextual data of two sides of a communication involving the individual who experiences states of pain/reduced function. In examples, such data can include one or more of: a second party's location during a phone call with the individual, the second party's phone number, the second party's length of acquaintance with the individual, and the second party's relationship to the individual (e.g., top contact, spouse, family member, friend, coworker, business associate, etc.).

Similar to Block S110, in relation to receiving the supplementary dataset, Block S120 can include transmitting the supplementary dataset from the mobile communication device S122 and/or any other suitable device (e.g., wearable device, biometric monitoring device, etc.) or system that serves as a source of supplementary data, to the computing system, as shown in FIG. 2. In transmitting the supplementary dataset, one or more sensor modules (e.g., sensor module of the mobile communication device, sensor module of a wearable computing device, sensor of a biometric monitoring device, etc.) can transmit data to the computing system by way of a wired and/or wireless data link (e.g., over Bluetooth, over Bluetooth LTE, etc.). As such, establishing of a communicable link (e.g., automatically, in response to a triggering condition, manually, etc.) can facilitate transmission of desired data in Block S120. However, Block S120 can include any other suitable variation of transmitting supplementary data, and/or receiving supplementary data.

1.2 Method—Active Data

Block S130 recites: receiving a survey dataset including responses, to at least one of a set of symptom-assessment surveys, associated with a set of time points of the time period, from the individual. Block S130 is preferably implemented at a module of the computing system described in relation to Blocks S110 and S120 above, but can additionally or alternatively be implemented at any other suitable system configured to receive survey data from one or more individuals. Block S130 functions to provide data related to a set of states associated with progression or other changes in state of a disorder contributing to increased pain and/or reduced function (e.g., rheumatic disorder, musculoskeletal disorder, chronic pain-related disorder, etc.), which can be associated with data from the log of use from Block S110 and/or supplementary data received in Block S120 to generate predictive models in the analysis of Block S140. Block S130 is preferably implemented at a module of the computing subsystem described in relation to Blocks S110 and S120 above, but can additionally or alternatively be implemented at any other suitable system configured to receive survey data from one or more patients. The survey dataset can include interview and/or self-reported information from the patient. Furthermore, the survey dataset preferably includes quantitative data, but can additionally or alternatively include qualitative data pertaining to a symptomatic state of the patient corresponding to at least a subset of the set of time points. Additionally or alternatively, Block S130 can include receiving clinical data (e.g., information gathered in a clinic or laboratory setting by a clinician).

The survey dataset can include interview and/or self-reported information from the individual. Furthermore, the survey dataset preferably includes quantitative data, but can additionally or alternatively include qualitative data pertaining to a pain-related state of the individual corresponding to at least a subset of the set of time points. Furthermore, while portions of the survey dataset preferably correspond to time points within the time period of Block S110, portions of the survey dataset can alternatively correspond to time points outside of the time period of Block S110 (e.g., as in a pre-screening or a post-screening survey). Additionally or alternatively, Block S130 can include receiving clinical data (e.g., information gathered in a clinic or laboratory setting by a clinician).

In Block S130, the set of time points can include uniformly or non-uniformly-spaced time points, and can be constrained within or extend beyond the time period of the log of use of the communication application of Block S110. As such, in variations, the set of time points can include regularly-spaced time points (e.g., time points spaced apart by an hour, by a day, by a week, by a month, etc.) with a suitable resolution for enabling detection of changes in a disorder state of the patient. Additionally or alternatively, provision of a survey and/or reception of responses to a survey can be triggered upon detection of an event of the patient (e.g., based upon data from sensors associated with the patient, based upon an output of an analysis of Block S140, etc.) or any other suitable change in state of the patient. For instance, sensors that enable detection of an injury of the patient (e.g., a fall), detection of changes in motion behavior (e.g., limping gait, reduction in mobility of extremities, etc.), and/or any other suitable sensors can facilitate triggering of survey provision and/or intervention in subsequent blocks of the method 100. Furthermore, for all time points of the set of time points, an identical subset of the set of symptom-assessment surveys can be provided to the patient; however, in alternative variations, different subsets of the set of symptom-assessment surveys can be provided to the patient at different time points of the set of time points.

In variations, the survey dataset can include responses to surveys configured to assess severity of disorder state in a patient along a spectrum, wherein the surveys transform qualitative information capturing a patient's symptoms, pain, and/or identified mobility states into quantitative data according to a response-scoring algorithm. The survey dataset can be based in self-report data from the patient and/or observational data of the patient. In examples, the set of symptom-assessment surveys can include surveys focused on pain assessment as derived from one or more of: a Wong-Baker FACES pain rating scale (with pain rated on a scale from 0-5, 5 being the most severe); a pain visual analog scale (VAS); a pain numeric rating scale (NRS); a verbal pain intensity scale; a brief pain inventory (BPI) tool; a rheumatic disease specific pain scale (DSPI) scored according to sum(X*Y), where X is the pain level on a 0-10 scale and Y is the percentage of this pain level in a given rheumatic disease group; an Osteoarthritis Research Society International-Outcome Measures in Rheumatoid Arthritis Clinical Trials (OARSI-OMERACT) tool; a survey describing pain location (e.g., with respect to a specific joint, with respect to location within a specific joint); a survey describing pain type (e.g., sharp pain, dull pain, etc.); a survey identifying pain cause (e.g., injury, aging, degeneration, etc.), a survey identifying pain frequency (e.g., with regard to regularity), a survey identifying patterns in pain (e.g., time of pain, weather-related pain, time-of-day-related pain, temperature-related pain, etc.), and any other suitable pain-related survey.

Additionally or alternatively, in examples, the set of symptom-assessment surveys can include surveys focused on the assessment of daily functioning and/or activity, as affected by a condition or disorder of the patient, as derived from one or more of: a physical activity scale (PAS) survey (with scores ranging from 0-10 on a continuous scale, where 10 is most severe); a PAS-II survey (with scores ranging from 0-10 on a continuous scale, where 10 is most severe); a Health Assessment Questionnaire (HAQ, HAQ-II) with scores ranging from 0-3 (with 3 being most severe) a disease activity index (DAI) tool (e.g., a CDAI tool with scores ranging from 0-76, 76 being most severe); and any other activity assessment tool. Additionally or alternatively, in examples, the set of symptom-assessment surveys can include surveys focused on symptom exhibition and severity assessment as derived from one or more of: a routine assessment of patient index data tool; a rheumatic arthritis disease activity score (DAS) survey (with scores ranging from 0 to 9.4, 9.4 being most severe); an arthritis impact measurement scale (AIMS); a British Isles Lupus Assessment Group (BILAG) tool; a systemic lupus erythematosus (SLE) activity questionnaire; an SLE symptom scale survey; and any other suitable survey or tool for assessing symptom exhibition and severity. Additionally or alternatively, the survey dataset can include responses to demographic (e.g., gender, marital status, ethnicity, socioeconomic status, education level, employment status, health status, sexual orientation, age, etc.) and/or behavioral traits (e.g., cigarette use, substance use, alcohol use, sexual activity, physical activity, etc.) of a patient. As such, the survey dataset can include quantitative scores of the patient for one or more subsets of surveys for each of the set of time points (or a subset of the set of time points). In an example of Block S120, the survey dataset comprises daily responses (e.g., for a period of 60 days) to a pain and physical functioning VAS, and weekly responses (e.g., for a period of 6 months) to a survey derived from a PAS-II tool.

In an example, the survey dataset comprises weekly responses (e.g., for a period of 6 months) to a PAS-II derived survey and weekly responses (e.g., for a period of 6 months) to a HAQ-II derived survey. In the example, the survey dataset further includes daily responses (e.g., for a period of 6 months) to one or more questions related to a Global assessment, and daily responses (e.g., for a period of 6 months) to a pain assessment survey. However, variations of the example can comprise any other suitable type of survey data, received in any other format or with any other suitable frequency.

In some variations, Block S130 can further include facilitating automatic provision of at least one of the set of symptom-assessment surveys at the mobile communication device(s) of the individual(s). As such, responses to one or more of the set of symptom-assessment surveys can be provided by user input at an electronic device (e.g., a mobile communication device of the patient), or automatically detected from user activity (e.g., using suitable sensors). Additionally or alternatively, provision of at least one of the set of symptom-assessment surveys can be performed manually by an entity (e.g., therapy providing entity, healthcare professional, relative, acquaintance, etc.) associated with an individual or received as derived from clinical data, with data generated from the survey(s) received in Block S130 by manual input. Additionally or alternatively, provision of at least one survey and/or reception of responses to the survey can be guided by way of an application executing at a device (e.g., mobile device, tablet) of a caretaker of the individual and/or the patient, wherein the application provides instruction (e.g., in an audio format, in a graphic format, in a text-based format, etc.) for providing the survey or the responses to the survey. Block S130 can, however, be implemented in any other suitable manner (e.g., by verbal communication over the phone, by verbal communication face-to-face, etc.).

Similar to Block S110, In relation to receiving the survey dataset, Block S130 can include transmitting the survey dataset from the mobile communication device S132 and/or any other suitable device or system that serves as a source of survey data, to the computing system over a communicable link, as shown in FIG. 2. In transmitting the survey dataset, one or more data storage modules (e.g., memory module of the mobile communication device, etc.) can transmit data to the computing system by way of a wired and/or wireless data link (e.g., over Bluetooth, over Bluetooth LTE, etc.). However, Block S130 can include another other suitable variation of transmitting survey data, and/or receiving survey data.

Blocks S110, S120, and S130 can thus provide passive data (e.g., unobtrusively collected data) and active data (e.g., survey data) that can be taken as inputs in Block S140 to generate analyses pertaining to present, past, and/or future pain-related states of a patient.

1.3 Method—Modeling and Predicting Pain-Related State

Block S140 recites: for at least a time point of the set of time points, transforming data from the log of use, the supplementary dataset, and the survey dataset into an analysis of a pain-related state of the individual associated with at least a portion of the time period. Block S140 functions to determine values of one or more pain-related parameters (e.g., in relation to symptom criticality) in association with at least one time point of the set of time points, based upon one or more of the log of use dataset, the supplementary dataset, and the survey dataset. Block S140 thus enables assessment of a past or current state of the individual related to pain and/or reduced function. Block S140 can additionally or alternatively predict risk that the individual will trend toward a different (e.g., worsened, improved, etc.) state at a future time point.

In the analysis, Block S140 can identify parameters/triggering events directly from passive data (i.e., the log of use dataset, the supplementary dataset) and/or from active data (i.e., the survey dataset), or can additionally or alternatively implement a predictive model that processes one or more of passive components (e.g., communication components, supplementary data components) and active components (e.g., survey components) to predict one or more present or future pain-related states of the individual, with training data. Additionally or alternatively, for individuals following a medication regimen for treatment or maintenance of health in relation to pain and/or other comorbid conditions, the analyses of Block S140 can include generation of an adherence model that assesses or predicts adherence of the patient to the medication regimen as an output of the analysis.

1.3.1 Pain-related State—Predictive Model

Preferably, generating a predictive model S142 in association with Block S140 includes utilization of one or more machine learning techniques and training data (e.g., from the patient, from a population of patients), data mining, and/or statistical approaches to generate more accurate models pertaining to the individual's pain and/or reduced function (e.g., over time, with aggregation of more data). As such, Block S142 is preferably implemented at a computing system configured to process data from the log of use dataset, the supplementary dataset, and the survey dataset. The computing system can be the same computing system associated with one or more of Blocks S110-S130 of the method 100, or can alternatively be any other suitable computing system.

In generating the predictive model, Block S142 preferably uses input data including communication behavior data from the log of use dataset, data from supplementary dataset, and data from the survey dataset to provide a set of feature vectors corresponding to time points of the time period. Feature selection approaches can include one or more of: factor analysis approaches that implement statistical methods to describe variability among observed features in terms of unobserved factors, in order to determine which features explain a high percentage of variation in data (e.g., with a principal component analysis); correlation feature selection (CFS) methods, consistency methods, relief methods, information gain methods, symmetrical uncertainty methods, and any other suitable methods of feature selection. In variations, feature selection approaches can be implemented for any passive data (e.g., communication data, mobility data), wherein a linking analysis of Block S140 is then used to determine associations between features of passive data and states of disorder determined from active data (e.g., survey response datasets). Analysis of the passive data in relation to the active data, with regard to feature selection and associations between passive and active data can, however, be performed in any other suitable manner.

In a specific example of model generation, Block S140 can include performing a principal component analysis (PCA) conducted with a screen plot (or any other suitable eigenvector output) and a Kaiser criterion of passive data components (e.g., from the log of use, from the supplementary data), together with a hierarchical cluster analysis using a Euclidian dissimilarity metric and the average linkage criterion with a Calinski/Haralasz rule for an optimal choice of number of clusters. Furthermore, the specific example implements generalized estimating equations (GEEs) to determine links between passive data components and other data components (e.g., survey dataset components). However, variations of Block S140 can be implemented using any other suitable technique, and in relation to any other suitable feature, as described in more detail below.

In one variation, the feature vectors can include features related to aggregate communication behavior, interaction diversity, mobility behavior (e.g., mobility radius as a measure of distance traveled by the individual within a given time period, such as the weekend), a number of missed calls, and a duration of time spent in a certain location (e.g., at home). In examples, feature vectors can be generated based upon aggregation of phone, text message, email, social networking, and/or other patient communication data for a particular period of time into one or more features for the patient for the particular time period. Furthermore, a feature can be specific to a day, a week, a month, a day period (e.g., morning, afternoon, evening, night), a time block during a day (e.g., one hour), a specific communication action (e.g., a single phone call, a set of communication actions of the same type (e.g., a set of phone calls within a two-hour period), all communications within a period of time, etc.). Additionally, combinations of features can be used in a feature vector. For example, one feature can include a weighted composite of the frequency, duration (i.e., length), timing (i.e., start and/or termination), and contact diversity of all outgoing voice (e.g., phone call) communications and a frequency, length, and timing and/or response time to (i.e., time to accept) incoming voice communications within the first period of time through a phone call application executing on the individual's mobile device. Feature vectors can additionally or alternatively include features based on analysis of voice communications, textual communications, mobile application activity usage, location data, and any other suitable data which can be based on variance, entropy, or other mathematical and probabilistic computations of basic data (e.g., a composite activity score, a composite socialization score, a work-life balance score, a quality-of-life score). However, the feature vectors can be determined in any other suitable manner.

In some variations, Block S142 can include utilizing statistics-based feature selection approaches to determine a subset of features from the log of use dataset, the supplementary dataset, and/or the survey dataset that have a high predictive power and/or high accuracy in generating one or more outputs of the predictive model. In examples, the approaches can implement one or more of: generalized estimating equations (GEEs); correlation-based feature selection (CFS), minimum redundancy maximum relevance (mRMR), Relief-F, symmetrical uncertainty, information gain, decision tree analysis (alternating decision tree analysis, best-first decision tree analysis, decision stump tree analysis, functional tree analysis, C4.5 decision tree analysis, repeated incremental pruning analysis, logistic alternating decision tree analysis, logistic model tree analysis, nearest neighbor generalized exemplar analysis, association analysis, divide-and-conquer analysis, random tree analysis, decision-regression tree analysis with reduced error pruning, ripple down rule analysis, classification and regression tree analysis) to reduce questions from provided surveys to a subset of effective questions, and other statistical methods and statistic fitting techniques to select a subset of features having high efficacy from the data collected in Blocks S110, S120, and/or S130. Additionally or alternatively, any assessment of redundancy or efficacy in a feature derived from data of Blocks S110, S120, and/or S130 can be used to provide a measure of confidence in an output of the predictive model from one or more input features. Furthermore, the statistical approach(es) of Block S142 can be used to strategically reduce portions of data collected based upon redundancy and/or lack of utility of the data. Even further, the statistical approaches/feature selection approaches can be used to entirely omit collection of portions of the data (e.g., responses to specific surveys or portions of surveys can render responses to other portions of surveys or other surveys redundant), in order to streamline the data collection in Blocks S110, S120, and/or S130.

In one example, a high degree of correlation (e.g., positive correlation) between responses to a weekly PAS-II assessment and a daily pain survey (e.g., a portion of recent responses to a daily pain survey in relation to a time point of interest, responses to the daily pain survey from 7 days before and 7 days after a session of responses to a PAS-II assessment) can be used to entirely omit provision of the weekly PAS-II assessment or portions of the PAS-II assessment, in lieu of the daily pain survey, due to redundancy in data collection, in variations of the method 100. In another example, a high degree of correlation (e.g., positive correlation) between responses to a weekly HAQ-II assessment and mobility data from the supplementary dataset can be used to entirely omit provision of the weekly HAQ-II assessment or portions of the HAQ-II assessment, in lieu of the mobility data, due to redundancy in data collection, in variations of the method 100. In still another example, a high degree of correlation (e.g., positive correlation) between a communication parameter derived from the log of use (e.g., call count predictability) and mobility data from the supplementary dataset can be used to entirely omit collection of data (e.g., call count data, mobility data) due to redundancy in data collection, in variations of the method 100. In still another example, a high degree of correlation (e.g., positive correlation) between a communication parameter derived from the log of use (e.g., predictability and entropy) and mobility data from the supplementary dataset can be used to entirely omit collection of data (e.g., call count data, mobility data) due to redundancy in data collection, in variations of the method 100.

In still other examples, correlations between active data and passive data including one or more of: positive correlations between pain survey score and overall use of a mobile communication device, positive correlations between pain survey score and contrasts between texting behavior and calling behavior (e.g., in relation to number of text messages sent and/or received, compared to number of phone calls sent and/or received, etc.), negative correlations between pain survey score and a phone calling component, positive correlations between daily pain survey score and number of outgoing SMS messages to a primary contact during peak hours, positive correlations between pain survey score and number of unreturned calls during off-peak hours, negative correlations between PAS-II assessment score and mobility, negative correlations between PAS-II assessment score and mobility radius, and negative correlations between PAS-II assessment score and call count predictability can be used to streamline data collection associated with Blocks S110, S120, and/or S130. However, any other suitable data derived from Blocks S110, S120, and S130 can be used to increase efficacy of data collection and/or determination of values of the pain-related state parameter in Block S142.

Additionally or alternatively, any assessment of redundancy or efficacy in a feature derived from data of Blocks S110, S120, and/or S130 can be used to provide a measure of confidence in outputs of the predictive model determined from the feature(s).

In some embodiments, the predictive model generated in Block S142 can process a set of feature vectors according to methods described in relation to the predictive modeling engine described in U.S. application Ser. No. 13/969,339, entitled "Method for Modeling Behavior and Health Changes" and filed on 16 Aug. 2014, which is incorporated herein in its entirety by this reference; however, the predictive model can alternatively be generated in any other suitable manner. As such, in variations of the model(s), a set of feature vectors from the input data can be processed according to a machine learning technique (e.g., support vector machine with a training dataset) to generate the value(s) of parameters associated with the pain-related state in relation to a time point. In one example, the predictive model can incorporate historical data from the individual (e.g., survey responses from a prior week, a history of passive data from the log of use, etc.), with more weight placed upon more recent data from Blocks S110-S130 in determination of a pain-related state associated with a time point by the predictive model; however, the predictive model can be implemented in any other suitable manner.

Furthermore, in extensions of the method 100 to a population of patients, the predictive model can be used to identify differences in passive data and/or active data, as associated with identified pain-related states, between different demographics of individuals. For instance, the predictive model can be used to identify sets of feature vectors and/or subsets of features (e.g., related to communication behavior, related to survey responses, related to mobility behavior, etc.) that have high efficacy in determining risk/severity for one or more of: different genders, different age groups, different employment statuses, different ethnicities, different nationalities, different socioeconomic classes, and any other suitable demographic difference.

While some variations of machine learning techniques are described above, in relation to generation of the predictive model, Block S140 can additionally or alternatively utilize any other suitable machine learning algorithms. In variations, the machine learning algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm.

1.3.2 Pain-Related State—Adherence Model

For patients taking medication to manage their pain, Block S140 can additionally or alternatively include processing datasets associated with Blocks S110, S120, and/or S130 with an adherence model S143 configured to assess and/or predict a state of adherence to a medication regimen by a patient. The adherence model can be an embodiment, variation, or example of an adherence model as described in U.S. application Ser. No. 13/969,339, entitled "Method for Modeling behavior and Health Changes", but can alternatively be any other suitable adherence model.

1.3.3 Pain-Related State—Parameters of Analysis and Criticality Assessment

Figure 3:
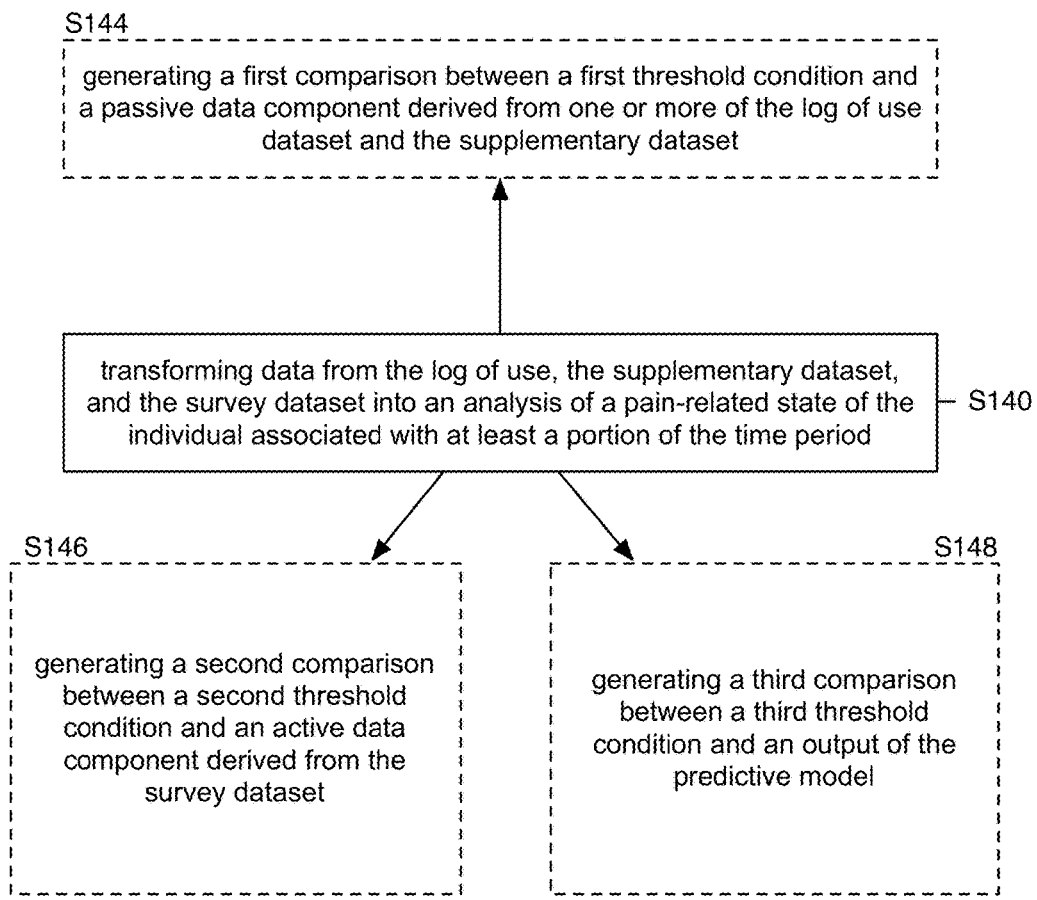
FIG. 3 is a flowchart of a variation of a portion of a method for modeling behavior and improving quality of life for an individual.

In generating the analysis of a pain-related state of the individual, Block S140 can include generating comparisons between different threshold conditions and one or more of: components of the log of use dataset, components of the supplementary dataset, components of the survey dataset, and outputs of the predictive model. As such, generating the analysis of the pain-related state of the individual in Block S140 can include one or more of: generating a first comparison between a first threshold condition and a passive data component derived from one or more of the log of use dataset and the supplementary dataset S144; generating a second comparison between a second threshold condition and an active data component derived from the survey dataset S146; and generating a third comparison between a third threshold condition and an output of the predictive model S148, as shown in FIG. 3. The comparisons of Blocks S144, S146, and/or S148 can thus be associated with parameters of the pain-related state of the individual used to assess criticality of the pain-related state of the individual, and/or to resolve a critical pain-related state of the individual in subsequent blocks of the method 100.

Figure 4A:
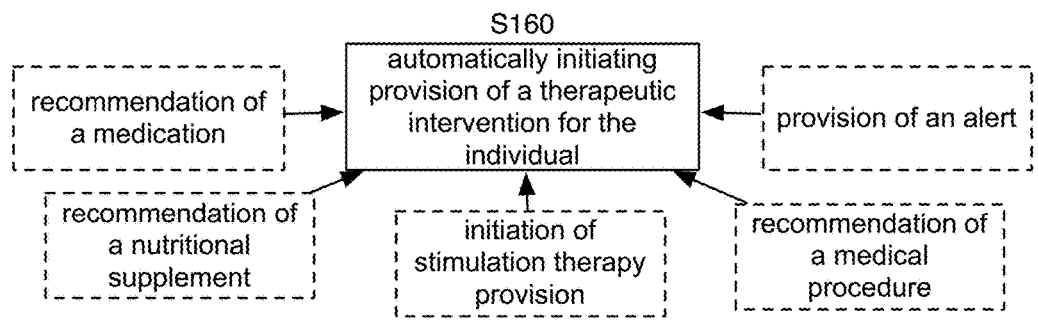
FIG. 4A depicts variations of intervention actions in an embodiment of a method for modeling behavior and improving quality of life for an individual.
Figure 4B:
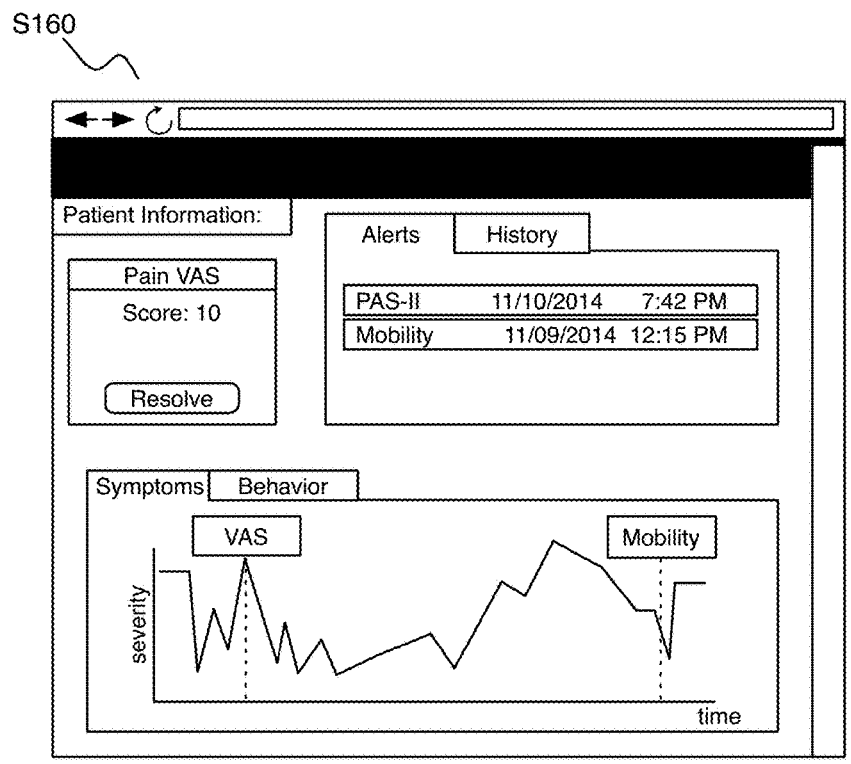
FIG. 4B depicts an example of a dashboard for providing an alert in an embodiment of a method for modeling behavior and improving quality of life for an individual.

Blocks S144, S146, and S148 thus function to process the outputs of Blocks S110-S130 of the method 100, such that the resolution actions of Block S150 are derived from at least one of an active component (i.e., a component derived from the survey response dataset), a passive component (e.g., a clinically-informed behavioral rule component determined by heuristics), and a component derived from the predictive model generated in Block S142. In particular, consideration of the active component, the passive component, and the component derived from the predictive model can significantly strengthen the efficacy of the resolution actions implemented in Block S150, examples of which are shown in FIGS. 4A and 4B. Furthermore, each of the active component, the passive component, and the predictive model component can have an associated time frame that is identical or different to time frames of analysis of the other components. Additionally, analysis of each of the active component, the passive component, and the predictive model component can occur within one or more time frames that are different from the time frame of an associated resolution action.

Block S144 recites: generating a first comparison between a first threshold condition and a passive data component derived from one or more of the log of use dataset and the supplementary dataset. In Block S144, generating the first threshold condition and a passive data element can comprise defining one or more categories of passive behaviors of the individual (e.g., related to lethargy, related to social isolation, related to physical isolation, related to evolution of the patient's support network, related to time spent at work, related to weekly behavioral patterns, etc.) based upon historical behavior of an individual within a duration of time (e.g., immediately prior 4-6 weeks of the individual's life). Then, Block S144 can include comparing the features of or evolution in the passive behavior(s) of the individual to the first threshold condition. In variations wherein the passive behaviors of the individual are monitored for a duration of time, the first threshold condition can additionally or alternatively include a frequency threshold and/or a frequency-within-a-duration-of-time threshold, in relation to generation of an indication based upon a passive data component.

In variations, the first threshold condition can include one or more of: a threshold condition of a mobility less than the $20^{th}$ percentile of values of a mobility-related parameter (e.g., mobility radius) for the time period (e.g., a time window of 5 days, including a specified number of values of the mobility-related parameter); a threshold condition of a mobility less than the $25^{th}$ percentile of values of a mobility-related parameter (e.g., mobility radius) for the time period (e.g., a time window of 5 days, including a specified number of values of the mobility-related parameter); a threshold condition of a set of values of a mobility-related parameter having low values for a number of consecutive days; a threshold condition of a number of unreturned calls greater than 2 for a number of consecutive days; a threshold condition of a number of unreturned calls greater than 2 for a number of consecutive days; a threshold condition of a duration of time spent at home having a value greater than 15 hours per day for a number of consecutive days; a threshold condition of a duration of time spent at home having a value greater than 22 hours per day for a day; a threshold condition of communication behavior less than the bottom $10^{th}$ percentile of values of communication-related parameter (e.g., communication diversity) for a number of consecutive days within a time period (e.g., a time window of 5 days, including a specified number of values of the communication-related parameter); any other suitable threshold condition; and any other suitable combination of threshold conditions.

In examples, the first comparison can thus facilitate identification of one or more of: a period of persistent reduction in mobility (e.g., a mobility radius below a threshold distance over a period of X consecutive days); a reduction in phone calling behavior (e.g., in terms of number of incoming calls compared to a threshold, in terms of number of outgoing calls compared to a threshold, in terms of number of missed calls compared to a threshold, in terms of length of incoming calls compared to a threshold, in terms of length of outgoing calls compared to a threshold); a reduction in text messaging behavior (e.g., in terms of number of incoming text messages compared to a threshold, in terms of number of outgoing text messages compared to a threshold, in terms of length of incoming text messages compared to a threshold, in terms of length of outgoing text messages compared to a threshold); a reduction in communication diversity (e.g., in terms of a diversity in individuals the individual communicates with); and any other suitable condition for indication generation. In particular, overall use of the mobile device by the individual can explain approximately 80% of the variation in individuals with critical symptoms vs. other individuals, contrast between texting behavior components and calling behavior components can explain approximately 20% of the variation in individuals with critical symptoms vs. other individuals (where individuals experiencing pain exhibit below a threshold amount of phone calling behavioral components, but compensate with increased text messaging behavioral components, and contrast between mobility behavior and calling duration can explain approximately 10% of the variation in individuals with critical symptoms vs. other individuals.

Thus, the first comparison of Block S144 can identify one or more of: a below-threshold condition for a phone calling parameter combined with an above-threshold condition for a text messaging parameter; an above-threshold condition for a mobility parameter combined with a below-threshold condition for travel radius; a below threshold condition for overall use of a mobile device; a below-threshold condition for a phone calling parameter; a below-threshold condition for mobility; and any other suitable comparison.

Block S146 recites: generating a second comparison between a second threshold condition and an active data component derived from the survey dataset. In Block S146, generating the second comparison between the second threshold condition and the active component derived from the survey response dataset can comprise assigning a score to one or more elements of the survey response dataset for a patient (e.g., based upon one instance of survey response provision, based upon multiple instances of survey response provision), and comparing the score(s) to the second threshold condition. In variations wherein the survey response dataset comprises responses to survey questions (e.g., a repeat set of survey questions) at each of a set of time points, the second threshold condition can additionally or alternatively include a frequency threshold and/or a frequency-within-a-duration-of-time threshold, in relation to generation of an indication based upon an active component. Furthermore, threshold conditions can be defined in relation to a baseline for each individual, based upon historical behavior of the individual.

As such, in variations, the second comparison can indicate one or more of: a score greater than a given threshold; a score greater than a given threshold for a certain duration of time; a change in score greater than a given threshold; a change in score greater than a given threshold as derived from the individual's historical score data; and any other suitable comparison. Furthermore, the comparison(s) can additionally or alternatively be generated based upon a percentile condition, a standard deviation (e.g., in score) condition, outlier detection analysis (e.g., of a score in relation to scores from the individual), and/or any other suitable condition, based upon analysis of a patient in isolation, based upon analysis of the individual's recent behavior in isolation, based upon analysis of a population of individuals, and/or any other suitable grouping of individuals.

In examples, the second comparison can facilitate identification of one or more of: a score for survey responses that surpasses a critical threshold score (e.g., a score above a critical value on a PAS-II survey); a change in survey score that surpasses a critical threshold; a set of scores for survey responses acquired at each of a set of time points within a duration of time, wherein a threshold proportion of the set of scores surpasses a critical threshold score (e.g., 2 of 3 surveys have scores above a critical threshold); a summation of scores for a set of scores for survey responses acquired at each of a set of time points that surpasses a critical threshold; a magnitude of difference in scores for survey responses acquired at different time points that surpasses a critical threshold (e.g., a PAS-II score greater than a previous score); a combination of scores for different surveys that surpasses a critical threshold for each of the different surveys; and any other suitable condition for indication generation.

Block S148 recites: generating a third comparison between a third threshold condition and an output of the predictive model. In Block S150, generating the third comparison between the third threshold condition and the output of the predictive model can comprise identification of a classification (e.g., a learned, complex, non-intuitive, and/or behavioral association exhibited by the individual), and comparing the classification to a threshold condition. In variations, a single feature and/or combinations of features derived from the log of use dataset, the supplementary dataset, and, the survey response dataset (e.g., with weighting among factors) can be compared to one or more threshold conditions, in identifying if an alert based upon the predictive model of Block S142 should be generated. In variations and examples, the third comparison can be generated as described in U.S. application Ser. No. 13/969,339, entitled "Method for Modeling Behavior and Health Changes" and filed on 16 Aug. 2014.

As such, in one example of Blocks S144, S146, and S148, accounting for a passive component, an active component, and a predictive model component, an indication can be based upon: a first passive component (e.g., related to contrasts in phone calling vs. text messaging communication behavior) generated from a first 2-day window of time, a second passive behavioral component (e.g., related to mobility of the individual) generated from a second window of time overlapping with the first 2-day window of time, scoring of a weekly survey, and a predictive model component for a time window of 14 days (e.g., overlapping with the period of the weekly survey), wherein the predictive model component implements an aggregated learning approach based upon multiple individual models (e.g., each assessing different parameters and/or different time periods of behavior of the individual).

The analyses of Block S140 can, however, include generation of any other suitable comparison and/or any other suitable output which serve as parameters of the pain-related state of the individual. Additionally or alternatively, the comparison(s) generated in Blocks S144, S146, and S148 can include identification or analysis of progress through a condition (e.g., in relation to persistence of symptoms, in relation to worsening of symptoms, in relation to improvement of symptoms, etc.).

1.4 Method—Resolution of Critical States of Pain/Reduced Function

Block S150 recites: generating an alert based upon one or more outputs of the analysis of Block S140, which functions to provide an indication that the individual is experiencing a critical state of pain or reduced function and/or is trending toward a critical state of pain/reduced function. Block S150 can thus include generating an alert upon detection, at the computing system performing the analysis, that one or more outputs (e.g., comparisons) from the analysis of the pain-related state satisfy associated threshold conditions. The alert of Block S150 can be an alert that prompts transmission of a notification to an entity associated with the individual, for instance, for therapeutic intervention. The alert can additionally or alternatively comprise an alert that serves as an input into a subsequent computer-implemented module for automatically providing an intervention to the individual, the intervention intended to improve the pain-related state of the individual.

As such, Block S150 can include Block S152, which recites: transmitting an alert based upon the analysis. Block S152 functions to alert at least one of an entity associated with the individual and/or the individual regarding a critical state of pain/reduced function that the individual has or will enter. Thus, Block S152 can provide an alert to an entity at a critical time point at which the alert has an increased or optimal effectiveness in preventing a regression in a pain-related state of the patient. In more detail, the alert can be transmitted upon enablement of a communicable link with at least one of the mobile device of the individual and a care provider computing device, wherein the communicable link is enabled in response to an output of Block S140. The alert can be a visual alert (e.g., text-based alert, graphic alert), audio alert, haptic alert, and/or any other suitable type of alert. In relation to an entity associated with the patient(s), the entity can include any one or more of: a caretaker, a healthcare provider, a relative (e.g., parent, significant other, etc.), and any other suitable entity associated with the patient. Furthermore, in relation to an entity associated with the patient(s), the alert(s) can be provided at a dashboard of an electronic interface (e.g., web portal, computing device, etc.) accessible by the entity. In the example shown in FIG. 4B, alert(s) of Block S152 can be provided at a dashboard of a web portal, wherein the alert(s) are text-based alerts including a type of alert (e.g., related to active data, related to passive data), a value of a pain-related state parameter associated with the alert, and a graphic that displays values of one or more scores of a survey (e.g., a daily mood survey) and/or a pain-related parameter over time. In the example, the graphic can include tags that facilitate identification of associations between metrics derived from active components and passive components (e.g., mobility parameter values in association with scores on a PAS-II assessment and/or scores on a daily pain survey). The dashboard can further provide an option to resolve the alert, wherein in examples, resolution of the alert can include any one or more of: triaging an individual's pain-related state, providing emotional support to the individual to improve the individual's pain-related state, assessing the level of follow up care needed to improve the individual's state (e.g., by facilitating an appointment with a primary care physician within 3 days, by alerting a friend of the patient, by facilitating immediate transfer of the individual to an emergency room, etc.), by providing a short term plan to the patient to improve the patient's pain-related state in an acute manner, by providing a long term plan to the individual that is configured to maintain a healthy state of the patient, and any other suitable resolving act (e.g., storing information/data resulting from a resolution action for future reference).

In relation to the comparison(s) of Blocks S144, S146, and S148, the alert can comprise an alert associated with active data (e.g., alerts related to PAS-II scores, alerts related to HAQ-II scores, scores on a daily pain VAS assessment, alerts related to daily pain scores, alerts related to medication adherence, etc.). Additionally or alternatively, the alert can comprise an alert associated with passive data (e.g., alerts related to reduction in movement in relation to a mobility parameter, alerts related to reduced phone-calling behavior paired with increased text-messaging behavior, alerts associated with reaching out to a support network associated with communication diversity, etc.). However, in variations of the specific examples noted above, the alerts can be associated with any other suitable form of active/passive data derived from other blocks of the method 100. As such, the alert can comprise any other suitable alert configured to facilitate improvement of the pain-related state of the patient.

Figure 4C:
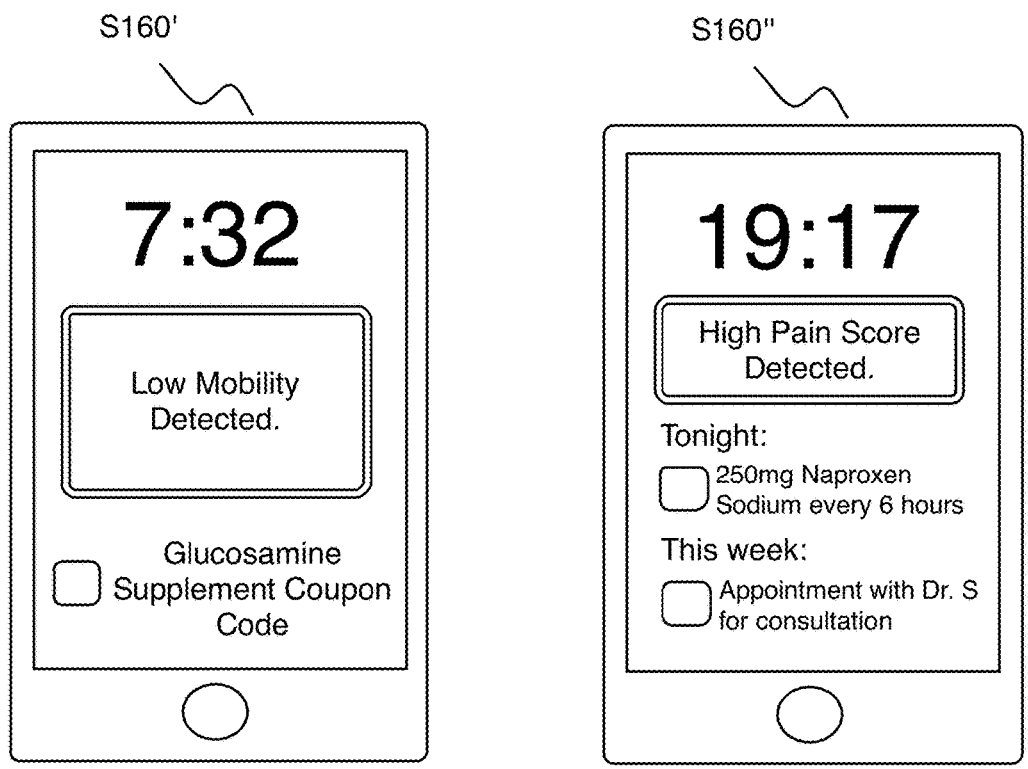
FIG. 4C depicts examples of interventions in an embodiment of a method for modeling behavior and improving quality of life for an individual.

In some variations, as shown in FIG. 1, the method 100 can further include Block S160, which recites: providing a notification to the individual, at the mobile communication device, in response to the analysis. Block S160 functions to provide information, advice, and/or motivational content to the individual so that the patient can improve his/her pain-related state, and/or maintain a healthy state. In variations of Block S160, the notifications can be provided with any suitable regular or non-regular frequency, can be provided with a sequence or in a random manner, can be triggered by an event, or can be provided in any other suitable manner. Furthermore, the notifications can include one or more of: a visual notification (e.g., text-based notification, graphic notification), an audio notification, a haptic notification, and any other suitable type of notification. In one example, a mobile device of a patient can download (e.g., upon initiation of download by one or more of the individual and an entity associated with the individual) and subsequently display the notification for the patient at a display of the mobile communication device, as shown in FIG. 4C, where the notifications are indicated as S160' and S160". The notifications can be personalized to the individual, or can be provided in the same manner to each of a population of individuals. In variations wherein the notifications are personalized to the individual, Block S160 can utilize a machine learning technique to identify the types of notifications that the patient responds positively to and/or negatively to, as assessed by patient outcomes in relation to pain-related state (e.g., indicated in values of the pain-related parameter).

In some variations, as shown in FIGS. 1 and 4A, the method 100 can further include Block S170, which recites: automatically initiating provision of a therapeutic intervention for the individual as facilitated by at at least one of the computing system and the mobile device. Block S170 functions to automatically and actively promote improvements to the individual's pain-related state, and/or to facilitate maintenance of a healthy state in the individual. In some variations, automatically initiating provision of a therapeutic intervention can include generating a therapy regimen configured to improve the pain-related state of the patient, based upon the analysis of Block S140. In associated variations, the therapy regimen can include therapeutic measures including any one or more of: automatic initiation of medication provision; automatic initiation of nutritional supplement provision; recommendation of a medical procedure; recommendation of physical therapy regimens; recommendation of massage provision; recommendation of stimulation therapy provision; and any other suitable intervention action.

In variations of Block S170 wherein intervention provision includes recommendation of a medication or initiation of medication distribution to the individual, recommended medications can be based upon severity of symptoms (e.g., acuteness of symptoms, type of symptoms), magnitude of a difference between a symptom criticality parameter and a threshold condition, type of disorder, as determined from a survey dataset, and any other suitable feature of the comparisons of Block S150. In variations, acuteness of symptoms associated with pain can trigger recommendation of a topical or oral pain medication (e.g., ibuprofen, aspirin, acetaminophen, hydrocodone, etc.) and/or an anti-inflammatory agent (e.g., NSAID, steroid). In variations, types of symptoms associated with a specific disorder can, for example, trigger recommendation of a disease-modifying antirheumatic drug (DMARD), a fibromyalgia medication (e.g., pregabalin, duloxetine hydrochloride, milnacipran HCl, etc.), an antimarial medication, an immunosuppressive medication, and any other suitable medication. In recommendation of a medication, Block S160 can facilitate provision of a prescription medication to the individual (e.g., by interfacing with a healthcare provider network and medication distribution entity to facilitate filling of a prescription for the patient). Additionally or alternatively, provision of a medication to the patient can be facilitated in any other suitable manner.

In variations of Block S170 wherein intervention provision includes recommendation of a nutritional supplement, recommended nutritional supplements can be based upon severity of symptoms (e.g., acuteness of symptoms, type of symptoms), magnitude of a difference between a symptom criticality parameter and a threshold condition), type of rheumatic or other disorder, as determined from a survey dataset, and any other suitable feature of the comparison of Block S150. For instance, for non-severe symptoms, recommended nutritional supplements can include joint-maintenance supplements including glucosamine supplements, chondroitin-sulfate supplements, hyaluronan supplements, calcium supplements, fish oil supplements, and/or any other suitable supplements. In examples of recommendation methods to promote adherence in taking a nutritional supplement, recommendation of the nutritional supplement can include provision of incentives (e.g., coupons) electronically, as shown in FIG. 4C, or non-electronically that motivate the patient to take the nutritional supplement.

In variations of Block S170 wherein intervention provision includes recommendation of a medical procedure, recommendations can be based upon severity of symptoms (e.g., acuteness of symptoms, type of symptoms), magnitude of a difference between a symptom criticality parameter and a threshold condition), type of rheumatic or other disorder, as determined from a survey dataset, and any other suitable feature of the comparison of Block S150. In promoting a given medical procedure, Block S170 can thus include one or more of: providing information to the patient regarding benefits and risks of the medical procedure (e.g., through a healthcare provider, through an application executing at an electronic device of the patient, etc.), facilitating the patient in making an appointment for consultation regarding the medical procedure, and any other suitable action that enables the patient to receive an appropriate treatment in a timely manner to prevent acceleration of progression of his/her disorder. In examples, recommended medical procedures can include one or more of: hyaluronan injections, allographic procedures to repair joint tissue, autologous procedures to repair joint tissue (e.g., autologous chondrocyte transplantation), microfracture procedures to promote joint healing with bone-marrow derived stem cells (BMSCs), joint replacement procedures (e.g., hip replacement, shoulder replacements, temporomandibular joint replacements, knee replacements), joint stabilization replacement procedures, defect repair procedures (e.g., using sutures, using adhesives, using chemical bonding procedures, etc.), and any other suitable medical procedure.

In variations of Block S170 wherein intervention provision includes recommendation of stimulation therapy provision, recommendations can be based upon severity of symptoms (e.g., acuteness of symptoms, type of symptoms), magnitude of a difference between a symptom criticality parameter and a threshold condition), type of rheumatic or other disorder, as determined from a survey dataset, and any other suitable feature of the comparison of Block S150. In promoting a given stimulation therapy, Block S170 can thus include recommendation or provision of a transcutaneous electrical nerve stimulation (TENS) treatments to the individual, with any suitable waveform characteristics (e.g., amplitude, phase, intermittency, etc.), any suitable electrode sites, and any other suitable TENS treatment configuration.

Furthermore, the therapy regimen and/or other therapeutic interventions can be provided using one or more of: healthcare provider interactions (e.g., therapeutic sessions with a counselor), pharmaceutical compound distributors, mobile application implemented methods, web browser-facilitated methods, and any other suitable avenue of therapy provision. The therapy regimen can additionally or alternatively be provided in a manner similar to that described in U.S. application Ser. No. 13/969,339, entitled "Method for Modeling Behavior and Health Changes", with therapy/treatment efficacy analyzed by a treatment regimen model and/or a treatment efficacy model. The therapy regimen can, however, be provided in any other suitable manner or assessed in any other suitable manner.

In some variations, the method 100 can further include Block S180, which recites: monitoring progress of the patient, after the intervention action has been enacted, based upon a second analysis derived from updates to at least one of the log of use, the survey dataset, and the supplementary dataset. With regard to Block S180, repeat instances of receiving log of use data, supplementary data (e.g., mobility-related data), and/or survey data, throughout the course of treatment of a patient's disorder, can contribute to monitoring of effectiveness of an intervention. In variations, analysis providing updated measures of symptom criticality parameters and/or comparisons (conducted in a similar manner to that of Block S140 and/or S150), throughout the course of treatment, can indicate improvement or worsening of an individual's disorder in relation to a recommended treatment. Thus, indications of improvement or worsening of symptoms of an individual's disorder can be used to promote continuance of an intervention method, adjustments to an intervention method, or completely change intervention for a patient. However, monitoring progress of the individual in Block S180 can be conducted in any other suitable manner.

The method 100 can, however, include any other suitable blocks or steps configured to model behavior and pain-related states, and/or improve a pain-related state of a patient. Furthermore, as a person skilled in the art will recognize from the previous detailed description and from the figures and claims, modifications and changes can be made to the method 100 without departing from the scope of the method 100.

2. System

Figure 5:
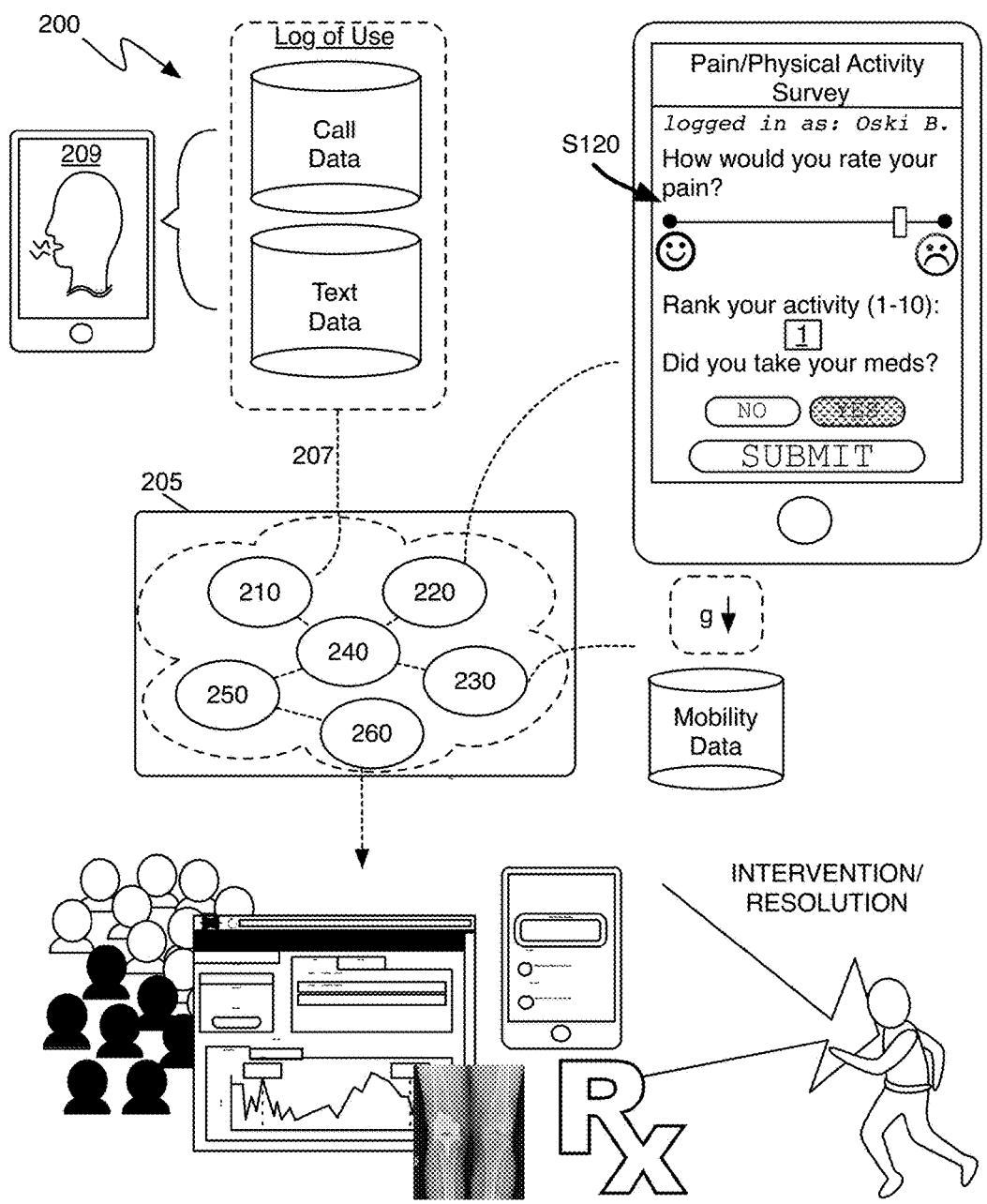
FIG. 5 depicts an embodiment of a system for modeling behavior and improving quality of life for an individual.

As shown in FIG. 5, a system 200 for modeling behavior and pain-related state of a individual includes: a processing system 205 including: an interface 207 with a communication data aggregation module executing on a mobile device 209 of the patient; a first module 210 configured to access a log of use of a communication application coupled to the communication data aggregation module on the mobile device by the individual within a time period; a second module 220 configured to receive a supplementary dataset characterizing activity of the patient in association with the time period; a third module 230 configured to receive a survey dataset including responses, to at least one of a set of symptom-assessment surveys, associated with a set of time points of the time period, from the individual; a fourth module 240 configured to transform data from the log of use, the survey dataset, and the supplementary dataset into an analysis of a pain-related state of the individual; and a fifth module 250 configured to generate an alert based upon one or more outputs of the analysis.

The system 200 functions to perform at least a portion of the method 100 described in Section 1 above, but can additionally or alternatively be configured to perform any other suitable method for modeling behavior and pain-related states of a patient. The system 200 is preferably configured to facilitate reception and processing of a combination of active data (e.g., survey responses) and passive data (e.g., unobtrusively collected communication behavior data, mobility data, etc.), but can additionally or alternatively be configured to receive and/or process any other suitable type of data. As such, the processing system 205 can be implemented on one or more computing systems including one or more of: a cloud-based computing system (e.g., Amazon EC3), a mainframe computing system, a grid-computing system, and any other suitable computing system. Furthermore, reception of data by the processing system 205 can occur over a wired connection and/or wirelessly (e.g., over the Internet, directly from a natively application executing on an electronic device of the patient, indirectly from a remote database receiving data from a device of the patient, etc.).

The processing system 205 and data handling by the modules of the processing system 205 are preferably adherent to health-related privacy laws (e.g., HIPAA), and are preferably configured to privatize and/or anonymize patient data according to encryption protocols. In an example, when an individual installs and/or authorizes collection and transmission of personal communication data by the system 200 through the native data collection application, the application can prompt the individual to create a profile or account. In the example, the account can be stored locally on the individual's mobile device 209 and/or remotely. Furthermore, data processed or produced by modules of the system 200 can be configured to facilitate storage of data locally (e.g., on the individual's mobile device, in a remote database), or in any other suitable manner. For example, private health-related patient data can be stored temporarily on the individual's mobile device in a locked and encrypted file folder on integrated or removable memory. In this example, the individual's data can be encrypted and uploaded to the remote database once a secure Internet connection is established. However, data can be stored on any other local device or remote data in any other suitable way and transmitted between the two over any other connection via any other suitable communication and/or encryption protocol. As such, the modules of the system 200 can be configured to perform embodiments, variations, and examples of the method 100 described above, in a manner that adheres to privacy-related health regulations.

The method 100 and/or system 200 of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for improving pain-related state determination for managing pain of an individual, the method comprising:

transmitting, from a communication module executing on a mobile device to a computing system, a log of use dataset associated with communication behavior of the individual during a time period, wherein the log of use dataset includes at least one of a phone calling component and a text messaging component;

at the computing system, receiving a motion supplementary dataset corresponding to a motion sensor of the mobile device, the motion supplementary dataset characterizing mobility of the individual in association with the time period;

collecting GPS data corresponding to a GPS sensor of the mobile device, the GPS data associated with location behavior of the individual in association with the time period;

within an application executing at the mobile device, generating a survey dataset upon retrieving responses provided by the individual to at least one of a set of surveys, associated with a set of time points of the time period;

selecting a patient subgroup for the individual from a first subgroup and a second subgroup based on the GPS data and the motion supplementary dataset, wherein the first subgroup is selected in response to the GPS data and the motion supplementary dataset indicating a first mobility behavior associated with the first subgroup, wherein the second subgroup is selected in response to the GPS data and the motion supplementary dataset indicating a second mobility behavior associated with the second subgroup, and wherein selection of the patient subgroup is operable to improve data storage, data retrieval, and the pain-related state determination;

at the computing system, generating a predictive model based on the selected patient subgroup, a passive dataset derived from the log of use dataset and the motion supplementary dataset, and the survey dataset;

determining a pain-related state of the individual, associated with at least a portion of the time period, from at least one of the passive dataset, the survey dataset, and an output of the predictive model;

at the computing system, upon detection that the pain-related state of the individual satisfies a threshold condition, enabling a communicable link with at least one of the mobile device of the individual and a care provider computing device; and by way of the communicable link, automatically initiating provision of a therapeutic intervention for improving a health outcome of the individual, by way of at least one of the computing system and the mobile device.

2. The method of claim 1, wherein transmitting the log of use dataset further includes: at the computing system, extracting, from the log of use dataset, a feature set including: a number of text messages sent by the individual, a length of text messages sent by the individual, a phone call duration, an outgoing call count, and a number of ignored calls.

3. The method of claim 2, wherein determining the pain-related state of the individual comprises transforming at least two components of the feature set into a comparison between text messaging behavior and phone calling behavior by the individual and detecting an increase in text messaging behavior over phone calling behavior, from the comparison.

4. The method of claim 1, wherein receiving the motion supplementary dataset includes extracting a mobility radius associated with at least one time point of the time period and derived from global positioning sensors of the mobile device.

5. The method of claim 4, wherein determining the pain-related state includes determining a mobility parameter, and wherein detecting satisfaction of the threshold condition includes 1) comparing the mobility parameter to a mobility radius threshold with an associated duration threshold, and 2) comparing a phone calling parameter from the log of use dataset to a phone calling parameter threshold.

6. The method of claim 1, wherein determining the pain-related state includes determining a parameter indicative of overall use of the mobile device by the individual from the log of use dataset, and wherein detecting satisfaction of the threshold condition includes comparing the parameter to a total use threshold within a duration of time.

7. The method of claim 1, wherein generating the survey dataset comprises providing, within an application executing at the mobile device, a set of surveys derived from at least one of: a Physical Activity Scale (PAS) survey, a Health Assessment Questionnaire (HAQ), and a pain and physical functioning visual assessment scale.

8. The method of claim 7, wherein providing the set of surveys includes automatically providing a first portion of the set of surveys within the application at a first subset of time points of the time period, and providing a second portion of the set of surveys within the application at a second subset of time points of the time period.

9. The method of claim 1, wherein automatically initiating provision of the therapeutic intervention includes at least one of: enabling a healthcare entity to contact the individual and providing health advice related to pain management to the individual within an application executing at the mobile device.

10. The method of claim 1, wherein automatically initiating provision of the therapeutic intervention comprises providing the healthcare entity with an electronically-implemented tool for contacting the individual.

11. A method for improving pain-related state determination for managing pain of an individual, the method comprising:
upon establishing communication between a computing system and a communication module of a mobile device of the individual, receiving a log of use dataset associated with communication behavior of the individual during a time period, at the computing system, wherein the log of use dataset includes at least one of a phone calling component and a text messaging component;
at the computing system, receiving a mobility sensor supplementary dataset corresponding to a mobility sensor of the mobile communication device, the mobility sensor supplementary dataset characterizing physical activity of the individual during the time period;
selecting a patient subgroup for the individual from a first subgroup and a second subgroup based on the mobility sensor supplementary dataset, wherein the first subgroup is selected in response to the mobility sensor supplementary dataset indicating a first mobility behavior associated with the first subgroup, wherein the second subgroup is selected in response to the mobility sensor supplementary dataset indicating a second mobility behavior associated with the second subgroup, and wherein selection of the patient subgroup is operable to improve data storage, data retrieval, and the pain-related state determination;
at the computing system, generating a predictive model of a pain-related state of the individual in association with at least a portion of the time period, based on the selected patient subgroup and the log of use dataset;
in response to an output of the predictive model that indicates that the pain-related state of the individual satisfies a threshold condition, enabling a communicable link with at least one of the mobile device of the individual and a care provider computing device; and
by way of the communicable link, automatically initiating provision of a therapeutic intervention for improving a health outcome of the individual.

12. The method of claim 11, further comprising: upon receiving the log of use dataset, extracting, from the log of use dataset, a feature set including: a number of text messages sent by the individual, a number of text messages received by the individual, a number of phone calls received by the individual, a length of text messages received by the individual, and a length of phone calls received by the individual.

13. The method of claim 12, further including: receiving a supplementary dataset, wherein receiving the supplementary dataset includes extracting a mobility radius associated with at least one time point of the time period and derived from global positioning sensors of the mobile device.

14. The method of claim 13, wherein generating the predictive model comprises processing information from the log of use dataset and the supplementary dataset with a principal component analysis.

15. The method of claim 13, wherein generating the predictive model further comprises processing information from the log of use dataset and the supplementary dataset, along with information derived from surveying the individual, with generalized estimating equations.

16. The method of claim 13, wherein generating the predictive model includes transforming at least two components of the feature set into a comparison between text messaging behavior and phone calling behavior by the individual and detecting an increase in text messaging behavior over phone calling behavior, from the comparison.

17. The method of claim 11, wherein automatically initiation provision of the therapeutic intervention comprises rendering an alert at a user interface of a dashboard of the care provider computing device, and wherein rendering the alert further includes providing, within the dashboard, an electronically-implemented tool for contacting the individual.

18. The method of claim 11, wherein generating the predictive model of the pain-related state of the individual includes generating an anticipated pain-related state of the individual at a future time point outside of the time period, and wherein the method further includes automatically initiating provision of the therapeutic intervention for the individual to prevent the anticipated pain-related state of the individual.

19. The method of claim 18, wherein the anticipated pain-related state is a state associated with a rheumatoid disorder, and wherein automatically initiating provision of the therapeutic intervention includes enabling a healthcare entity to contact the individual proximal in time to a future time point associated with the anticipated state.

20. The method of claim 11, wherein automatically initiating provision of the therapeutic intervention comprises determining parameters of a transcutaneous electrical nerve stimulation (TENS) treatment appropriate for the individual.

* * * * *